United States Patent

Kramer et al.

Patent Number: 6,072,180
Date of Patent: Jun. 6, 2000

[54] NON-INVASIVE INFRARED ABSORPTION SPECTROMETER FOR THE GENERATION AND CAPTURE OF THERMAL GRADIENT SPECTRA FROM LIVING TISSUE

[75] Inventors: Charles E. Kramer, Poway; Bernhard B. Sterling, Danville; James R. Braig, Alameda, all of Calif.; Daniel S. Goldberger, Boulder, Colo.; Arthur M. Shulenberger, Brisbane, Calif.; Rick Trebino, Livermore, Calif.; Richard A. King, Berkeley, Calif.

[73] Assignee: Optiscan Biomedical Corporation, Almaeda, Calif.

[21] Appl. No.: 08/816,723

[22] Filed: Mar. 12, 1997

Related U.S. Application Data

[63] Continuation-in-part of application No. 08/544,267, Oct. 17, 1995, abandoned.

[51] Int. Cl.[7] .......................... G01N 21/35; G01N 21/71
[52] U.S. Cl. ................................. 250/341.6; 250/339.03
[58] Field of Search .............................. 250/339.03, 341.6

[56] References Cited

U.S. PATENT DOCUMENTS

| | | |
|---|---|---|
| 3,958,560 | 5/1976 | March . |
| 4,223,680 | 9/1980 | Jöbsis . |
| 4,281,645 | 8/1981 | Jöbsis . |
| 4,407,290 | 10/1983 | Wilber . |
| 4,714,080 | 12/1987 | Edgar, Jr. et al. . |
| 4,766,315 | 8/1988 | Hellstrom et al. ................. 250/339.02 |
| 4,819,752 | 4/1989 | Zelin . |
| 4,934,372 | 6/1990 | Corenman et al. . |
| 5,009,230 | 4/1991 | Hutchinson . |
| 5,028,787 | 7/1991 | Rosenthal et al. . |
| 5,070,242 | 12/1991 | McClelland et al. .............. 250/339.03 |
| 5,070,874 | 12/1991 | Barnes et al. . |
| 5,075,552 | 12/1991 | McClelland et al. . |
| 5,081,998 | 1/1992 | Yelderman et al. . |
| 5,095,913 | 3/1992 | Yelderman et al. . |
| 5,137,023 | 8/1992 | Mendelson et al. . |
| 5,159,936 | 11/1992 | Yelderman et al. . |
| 5,191,215 | 3/1993 | McClelland et al. . |
| 5,313,941 | 5/1994 | Braig et al. . |
| 5,383,452 | 1/1995 | Buchert . |
| 5,666,956 | 9/1997 | Buchert . |

FOREIGN PATENT DOCUMENTS 612271  7/1979  Switzerland .

Primary Examiner—Constantine Hannaher
Attorney, Agent, or Firm—LaRiviere, Grubman & Payne, LLP

[57] ABSTRACT

A spectrometer for the non-invasive generation and capture of thermal gradient spectra from human or animal tissue. The spectrometer includes an infrared transmissive thermal mass for inducing a transient temperature gradient in the tissue by means of conductive heat transfer with the tissue, and cooling means in operative combination with the thermal mass for cooling the thermal mass. Also provided is an infrared sensor means for detecting infrared emissions emanating from the tissue as the transient temperature gradient progresses into the tissue, and for providing output signals proportional to the detected infrared emissions. Data capture means is provided for sampling the output signals received from the infrared sensor means as the transient temperature gradient progresses into the tissue.

29 Claims, 11 Drawing Sheets

Glucose Spectra 10,000 mg/dl glucose; sigmoidal glucose gradient at 40 microns

NON-INVASIVE INFRARED ABSORPTION SPECTROMETER FOR THE GENERATION AND CAPTURE OF THERMAL GRADIENT SPECTRA FROM LIVING TISSUE

This application is a continuation-in-part of application Ser. No. 08/544,267, filed on Oct. 17, 1995, now abandoned.

TECHNICAL FIELD

The present invention relates to a method and apparatus for inducing a transient thermal gradient in human or animal tissue, and for obtaining thermal gradient spectra from the tissue as the thermal gradient propagates through the tissue. The resulting thermal gradient spectra can then be converted to conventional infrared spectra, which in turn can be used to determine concentrations of substances which are present in the tissue, such as glucose.

BACKGROUND OF THE INVENTION

Infrared spectrometry is an accepted and widely practiced technique for identification and quantification of compounds. The most common method of analysis is via a transmission spectra. In this method an analysis beam of infrared light is passed through the substance being analyzed. The sample substance absorbs light in varying amounts at different wavelengths producing a transmission spectra which is a graph of the energy passed through the sample vs. wavelength. In this method the substance being analyzed is contained in a "cell" and placed inside the instrument for scanning. The analysis beam enters one side of the cell and exits the other. This is clearly an in-vitro technique not suitable for non-invasive measurements.

In another common technique the phenomena of Attenuated Total Internal Reflection (ATIR) is used. In this technique the sample is deposited on a plate fabricated of infrared transmissive material. The analysis beam is reflected off of this plate and back into the analyzer. At the point of reflection a portion of the analysis beam (evanescence wave) actually travels through the plate and interacts with the sample, then this portion of the beam returns to the analyzer along with the other reflected beam. A 1000 cm-1 infrared ATIR beam typically penetrates 10 microns into the sample under study. This technique, although potentially noninvasive, is not suitable for studying the composition of deeper layers of a material.

Transmission mode measurements are ideal for gasses which transmit a large percentage of incident energy and can be easily contained in a cell. Solids and liquids are traditionally measured by using either very thin transmission mode samples or the ATIR technique. The transmission mode technique has severe limitations if the substance being measured is very dense in the wavelength region of interest.

For instance if one was analyzing glucose dissolved in water or human blood the 9 to 10 micron wavelength region would be ideal however the incident analysis beam would be totally absorbed with less than 200 microns of path length. Maintaining a sample of such thin proportions is difficult. In such a case of high absorption, the ATIR technique might be useful, however, in that technique the analysis beam passes only approximately 10 microns into the substance being analyzed. The technique is useful only if the properties being measured exist very near the surface of the sample.

The transmission and ATIR mode analysis are very useful in the laboratory however if one wishes to measure something in-vivo such as glucose in blood where the most peripheral capillaries are covered by typically 40 microns of epithelial tissue clearly neither techniques are adequate.

Infrared detection techniques are widely used for the calculation of oxygen saturation and the concentration of other blood constituents. For example, noninvasive pulse oximeters have been used to measure absorption signals at two or more visible and/or near infrared wavelengths and to process the collected data to obtain composite pulsatile flow data of a person's blood. Sample pulse oximeters of this type are described by Corenman et al. in U.S. Pat. No. 4,934,372; by Edgar, Jr. et al. in U.S. Pat. No. 4,714,080; and by Zelin in U.S. Pat. No. 4,819,752.

Infrared detection techniques have also been used to calculate the concentrations of constituents such as nitrous oxide and carbon dioxide in the expired airstream of a patient. For example, Yelderman et al. describe in U.S. Pat. Nos. 5,081,998 and 5,095,913 techniques for using infrared light to noninvasively measure the absolute concentrations of the constituents of the respiratory airstream of a patient by placing an infrared transmission/detection device on the artificial airway of the patient. These infrared detection techniques and those described above have proven to be quite accurate in the determination of arterial blood oxygen saturation, the patient's pulse, and the concentrations of carbon dioxide, nitrous oxide and other respiratory constituents.

Spectrophotometric methods have also been used to non-invasively monitor the oxidative metabolism of body organs in vivo using measuring and reference wavelengths in the near infrared region. For example, Jobsis describes in U.S. Pat. Nos. 4,223,680 and 4,281,645 a technique in which infrared wavelengths in the range of 700–1300 nm are used to monitor oxygen sufficiency in an organ such as the brain or heart of a living human or animal. In addition, Wilber describes in U.S. Pat. No. 4,407,290 a technique in which visible and near infrared light emitting diodes and detection circuitry are used to noninvasively measure changes in blood thickness of predetermined blood constituents relative to total change in blood thickness at a test area so as to determine the concentration of such constituents in the blood. Such constituents include hemoglobin and oxyhemoglobin, and the measured concentrations are used to determine the oxygen saturation of the blood. Wilber further suggests at columns 11–12 that such techniques may be extended to the measurement of glucose in the bloodstream; however, Wilber does not tell how to make such measurements, what wavelengths of energy to use, or the form of the mathematics necessary for the calculation of glucose concentration.

Long wavelength spectroscopic glucose monitoring techniques using infrared light are presently believed to be the most accurate and are the subject of the present application. Unlike the noninvasive oxygen saturation measurement techniques described above, prior art spectroscopic glucose monitoring techniques have typically used extra-corporeal "flow through" cells that allow continuous measurements using infrared light. Indeed, attenuated total internal reflection (ATIR) cells have been employed in the long wavelength infrared to measure the glucose content of extracted blood samples. However, such techniques require samples of blood to be taken from the person and are thus undesirable for widespread consumer use.

Laser Raman Spectroscopy is another spectroscopic technique which uses a visible spectrum range stimulus and the visible red spectrum for measurement. As with ATIR cells, extra-corporeal blood is also used with Raman Technology. The Raman technique is based upon the principle that if excited with a specific wavelength certain constituents will re-emit optical energy at composition dependent specific wavelengths. Over the entire visible spectrum range whole blood has a high degree of absorption.

Another class of spectroscopic technique is described by Barnes in U.S. Pat. No. 5,070,874. According to this technique, often referred to as noninvasive near infrared spectroscopy, light is passed though a finger or suitable appendage and monitored upon exit for measuring glucose levels in vivo. Unfortunately, this technique suffers from two sources of inaccuracy: tissue interference and lack of specificity. Moreover, while the near infrared wavelengths used are easily and economically generated by light emitting diodes (LEDs) and solid state lasers, and easily transmitted through human tissue, they are not in a range specifically absorbed by glucose. This lack of "fingerprint" absorbance and interference from tissue pigment and condition render the technique unsuitable for accurate concentration determination but possibly acceptable for trending if stability can be maintained.

In an attempt to overcome the limitations of near infrared wavelengths Kaiser describes in Swiss Patent No. 612,271 a technique in which a high power infrared laser is used as the radiation source for measuring glucose concentration in a measuring cell. The measuring cell consists of an ATIR measuring prism which is wetted by the person's blood and an ATIR reference prism which is wetted with a comparison solution. $CO_2$ laser radiation, typically at 10.5 microns wavelength, is led through the measuring cell and gathered before striking a signal processing device. A chopper placed before the measuring cell allows two voltages to be obtained corresponding to the signal from the sample and the reference prisms.

Due to absorption corresponding to the concentration of the substance measured in the blood, the difference between the resulting voltages is proportional to the concentration. Unfortunately, the infrared laser used by Kaiser needs to be very powerful to get the 10.5 micron energy to pass through the blood and has the undesirable side effect of heating the blood, which may be harmful to the person if the blood were returned to the body. Although Kaiser suggests that over heating the blood may be prevented by using extra-corporeal cuvettes of venous blood and high blood flow rates, Kaiser does not describe a noninvasive technique for measuring glucose concentration.

March in U.S. Pat. No. 3,958,560 describes a "non invasive" automatic glucose sensor system which senses the rotation of polarized near infrared light which has passed through the cornea of the eye. March's glucose sensor fits over the eyeball between the eyelid and the cornea and measures glucose as a function of the amount of radiation detected at the detector on one side of the person's cornea. Unfortunately, while such a technique does not require the withdrawal of blood and is thus "noninvasive", the sensor may cause considerable discomfort to the person because of the need to place it on the person's eye. A more accurate and less intrusive system is desired.

Hutchinson describes in U.S. Pat. No. 5,009,230 a personal glucose monitor which also uses polarized near infrared light to noninvasively detect glucose concentrations in the person's bloodstream. The amount of rotation imparted on the polarized light beam is measured as it passes through a vascularized portion of the body for measuring the glucose concentration in that portion of the body. Although the monitor described by Hutchinson need not be mounted on the person's eye, the accuracy of the measurement is limited by the relatively minimal and non specific absorption of glucose in the 940–1000 nm range, dictated by the requirement of polarization, used by Hutchinson.

Mendelson et al. in U.S. Pat. No. 5,137,023 also found that wavelengths in the near infrared range are useful for noninvasively measuring the concentration of an analyte such as glucose using pulsatile photoplethysmography. In particular, Mendelson et al. describes a glucose measuring instrument which uses the principles of transmission and reflection photoplethysmography, whereby glucose measurement is made by analyzing either the differences or the ratio of two different near infrared radiation sources that are either transmitted through an appendage or reflected from a tissue surface before and after blood volume change occurs in the systolic and diastolic phases of the cardiac cycle. The technique of photoplethysmography can thus be used to adjust the light intensity to account for errors introduced by excessive tissue absorptions. However, despite the assertions by Mendelson et al., the wavelengths in the near infrared (below 2500 nm) are not strongly absorbed by glucose yet are susceptible to interference from other compounds in the blood and thus cannot yield sufficiently accurate measurements.

Rosenthal et al. in U.S. Pat. No. 5,028,787 disclose a noninvasive blood glucose monitor which also uses infrared energy in the near infrared range (600–1100 nm) to measure glucose. However, as with the above-mentioned devices, these wavelengths are not in the primary absorption range of glucose and, accordingly, the absorption at these wavelengths is relatively weak. A more accurate glucose measuring technique which monitors glucose absorption in its primary absorption range is desirable.

As with other molecules, glucose more readily absorbs infrared light at certain frequencies because of the characteristic and essential infrared absorption wavelengths of its covalent bonds. For example, as described by Hendrickson et al. in *Organic Chemistry,* 3rd Edition, McGraw-Hill Book Company, Chapter 7. Section 7-5, pages 256–264, C—C, C—N, C—O and other single carbon bonds have characteristic absorption wavelengths in the 6.5–15 micron range. Due to the presence of such bonds in glucose, infrared absorption by glucose is particularly distinctive in the far infrared. Despite these characteristics, few have suggested measuring glucose concentration in the middle to far infrared range, likely due to the strong tissue absorption that would attenuate signals in that range.

In one known example of such teachings, Mueller describes in WO 81/00622 a method and device for determining the concentration of metabolites in blood using spectroscopic techniques for wavelengths in the far infrared range. In particular, Mueller teaches the feasibility of measuring glucose in extra-corporeal blood samples using a 9.1 um absorption wavelength and a 10.5 um reference wavelength for stabilizing the absorption reading. However, Mueller does not describe how such wavelengths may be used in vivo to measure glucose concentration noninvasively while overcoming the above-mentioned tissue absorption problems. Without overcoming the large absorption by tissue in the 9 to 10 micron wavelength range, typically 90% absorption within 30 micron of optical path in human tissue, high power infrared energy must be incident on the measurement site which can cause tissue damage and discomfort.

On the other hand, infrared emissions of bodies have been used to determine the absolute temperatures of those bodies. For example, some of the present inventors disclose a tympanic thermometer in U.S. Pat. No. 5,159,936 which measures the absolute temperature of a person from the sum total of all infrared energy emissions from the person's tympanic membrane. However, such broadband infrared energy emissions have not been used to perform constituent composition and concentration analysis.

McClelland in U.S. Pat. No. 5,070,242, No. 5,075,552, and No. 5,191,215 describes a method for applying a cooling medium to cool a thin surface layer portion of the material and to transiently generate a temperature differential between the thin surface layer portion and the lower portion of the material sufficient to alter the thermal infrared emission spectrum of the body from the black-body thermal infrared emission of the material. The altered thermal emission spectrum is detected while the emission spectrum is sufficiently free of self-absorption by the material of the emitted infrared radiation. The detection is effected prior to the temperature differential propagating into the lower portion of the material to an extent such that the altered thermal infrared emission spectrum is no longer sufficiently free of self-absorption by the material of emitted infrared radiation. By such detection, the detected altered thermal infrared emission spectrum is indicative of the characteristics relating to the molecular composition of the homogenous material.

Another prior art device developed by some of the same inventors is disclosed in U.S. Pat. No. 5,313,941 by Braig et al. In this device high intensity infrared energy of the optimal wavelength, 3 to 12 microns is passed through the finger to make a transmission mode measurement. This device requires high incident energy levels to overcome the high absorbance of tissue in this wavelength band. In this device the energy is pulsed at very low duty cycles to avoid overheating the skin.

A technique for the non invasive measurement of physiological constituents, specifically glucose, must address the problems that tissue is heterogeneous in composition with the tissue layers containing the physiological concentration of interest laying 40–150 microns below the surface. Furthermore, the technique must assure a safe and effective measurement that will not cause temporary or permanent damage to the surface or underlying tissues in the measurement site nor cause discomfort to the human subject. The technique must also overcome the potential problem that glucose and other physiological constituents are present in combination with a number of other similar molecules and must be distinguished for accurate quantification. Ideally such a technique would not require a high power source of infrared energy so that a device could be made portable and lightweight.

Accordingly, what is needed is a system and method to overcome at least some of the problems associated with prior art techniques, and to address the constraints cited above. The present invention addresses such a need.

SUMMARY OF THE INVENTION

According to the invention there is provided a spectrometer for the non-invasive generation and capture of thermal gradient spectra from human or animal tissue. The spectrometer includes an infrared transmissive thermal mass for inducing a transient temperature gradient in the tissue by means of conductive heat transfer with the tissue, and cooling means in operative combination with the thermal mass for cooling the thermal mass.

Also provided is an infrared sensor means for detecting infrared emissions emanating from the tissue as the transient temperature gradient progresses into the tissue, and for providing output signals proportional to the detected infrared emissions. Data capture means is provided for sampling the output signals received from the infrared sensor means as the transient temperature gradient progresses into the tissue.

The invention also provides a method for the non-invasive generation and capture of thermal gradient spectra from living tissue. The method comprises the steps of:

cooling an infrared transmissive mass;

placing the infrared transmissive mass into a conductive heat transfer relationship with the tissue thereby to generate a transient temperature gradient in the tissue;

detecting infrared emissions emanating from the tissue and passing through the infrared transmissive mass;

providing output signals proportional to the detected infrared emissions; and sampling the output signals as the transient temperature gradient progresses into the tissue.

Other features of the invention are disclosed or apparent in the section entitled "BEST MODE OF CARRYING OUT THE INVENTION"

BRIEF DESCRIPTION OF THE DRAWINGS

For fuller understanding of the present invention, reference is made to the accompanying drawings in the following detailed description of the Best Mode of Carrying Out the Invention. In the drawings.

BEST MODE OF CARRYING OUT THE INVENTION

The present invention relates to the measurement of infrared energy absorption in a heterogeneous body. The following description is presented to enable one of ordinary skill in the art to make and use the invention as provided in the context of a particular application and its requirements. Various modifications to the preferred embodiments will be readily apparent to those skilled in the art, and the generic principles defined here may be applied to other embodiments. Thus, the present invention is not intended to be limited to the embodiments shown, but is to be accorded the widest scope consistent with the principles and novel features disclosed herein.

Any object at a temperature above absolute zero (−273.16 Degrees Celsius) emits infrared energy. The energy density of such emissions is described by Planck's law:

$$W = em * Fn(u,t)$$

Where:
W=energy in watts/cm 2 per micron
em=emissivity
Fn=a mathematical function with variables u and t
u=wavelength of emitted energy, in microns
t=temperature of emitting body, in Kelvin
The full form of this equation is:

$$W = em *(3.74E4/\{u\ 5*[(\exp(1.438E4/(u*t))-1]\})$$

Figure 1:
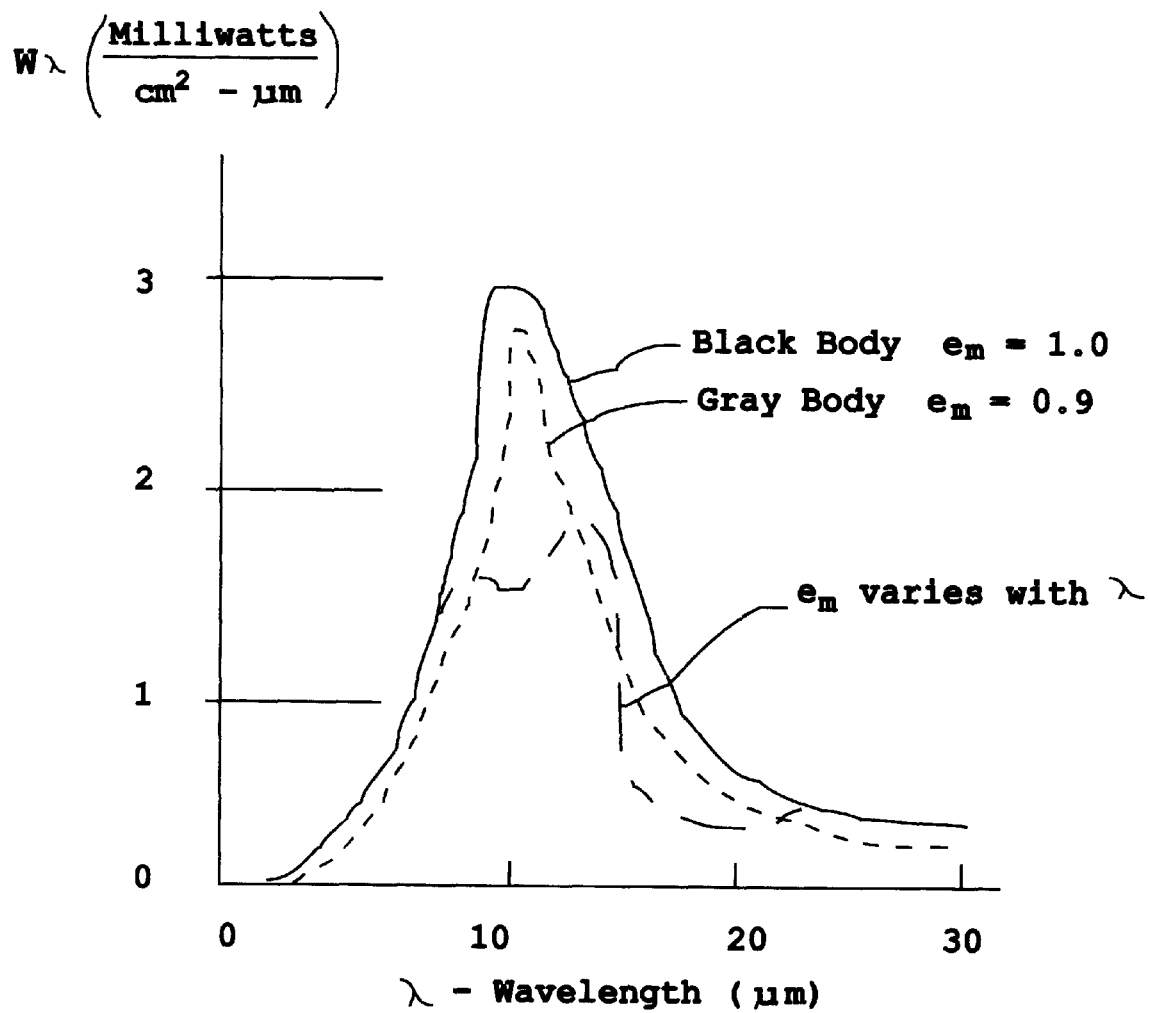
FIG. 1 is a graph of a black body emission spectra from a heated body.

The graph of these emissions vs. wavelength is often referred to as a blackbody curve. Such a curve is shown in FIG. 1. Theoretically, a body with emissivity 1.0 would exhibit this emission spectra according to Planck's law. Many objects have emissivities close to 1.0. Human tissue for instance has an emissivity of approximately 0.9 to 0.98. It is well known that infrared emissions from the human body obey Planck's law and yield a black body type emission spectra.

Although a human body may emit energy that follows Planck's law, Planck's law does not completely describe the sum total of all energy emitted from a human body for two reasons:

1. The layers of the tissue and body fluids are selectively absorptive to some wavelengths of infrared energy. Thus layers of tissue and blood or other fluids may selectively absorb energy emitted by the deeper layers before that energy can reach the surface of the skin.
2. There is a temperature gradient within a body, the deeper layers being warmer than the outer layers which causes further deviation from the theoretical black body emissions.

Whenever these two conditions exist naturally, or can be forced to exist, Applicants have determined that a composition dependent absorption spectra can be constructed from proper analysis of the total energy emitted from the body. For heterogeneous bodies, composition may be depth dependent and conversely, absorption spectra generated from deeper layers can contain sufficient composition information to allow quantification of the concentrations of individual constituents at that depth into the tissue. This is possible when a temperature gradient either occurs or is induced in the body. The slope of the temperature gradient is such that the temperature is cooler at the surface of the body closer to an infrared detector than at a more distant location from the detector, typically deep within the body.

The present invention uses the natural temperature within the body as the source of the infrared emissions. The natural emissions of the present invention are merely black body emissions fitting Planck's equation—they do not contain any composition dependent structure. As will be explained in more detail below, as these deep infrared emissions pass through layers of tissue that are at a lower temperature than the deeper emitting layer they are selectively self absorbed. This selective self absorption produces bands of reduced energy in the resulting emission spectra when the energy finally exits the material under study. The spectra containing the bands where energy has been self absorbed is called an absorption spectra.

The present invention employs cooling to promote "self-absorption" by letting the temperature gradient propagate to selected layers typically between 40 and 150 microns below the surface. When the temperature gradient has sufficiently propagated, the present technique can, noninvasively, deliver absorption spectra of the tissue, blood, and interstitial fluid containing glucose. The present invention can deliver precise information about the composition of individual layers deep within a heterogeneous body of material by measuring the absorption spectra at different times as a temperature gradient propagates from the surface to deep within the material under test.

A conceptual explanation for the phenomenon in accordance with the present invention will be described herein below. Consider for the sake of explanation the case of human skin. It is known that in a typical forearm the core temperature is approximately 37° C. and the external surface is typically at 30° C.

Figure 2:
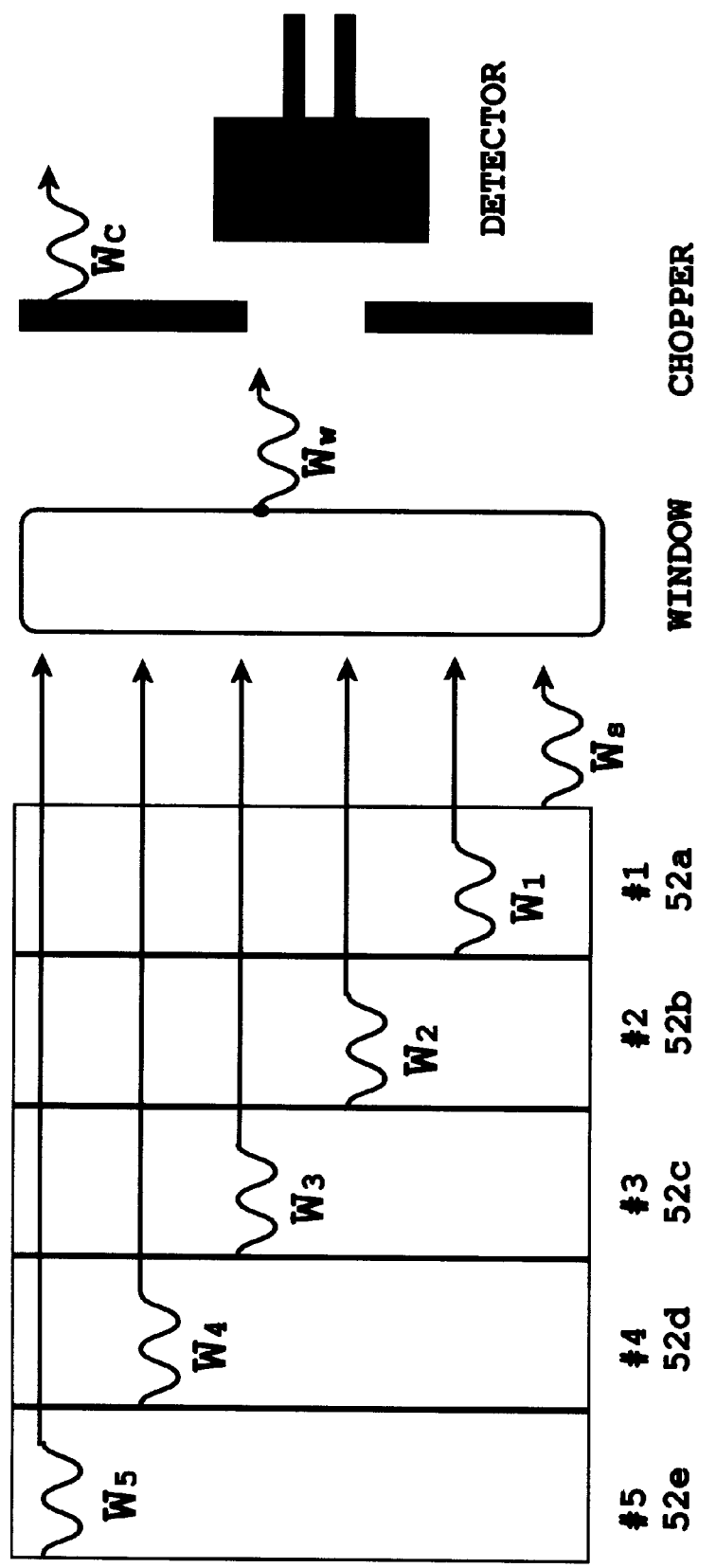
FIG. 2 is a block diagram of a typical body that includes multiple layers.

To simplify our conceptual model consider that the skin is made of many layers each approximately 10 microns thick. Let's further simplify our model in FIG. 2 by assuming that each layer 52a–52e in the model emits energy according to Planck's equation based on the temperature of that layer 52a–52e. A detector system 54 looking from outside can observe that radiation. The outermost layer 52a emits energy that travels directly to the detector 54, energy from the outer layer 52a does not pass through any other layer 52b–52e on its route to the detector 54. Energy from the second layer 52b inward must pass through the first layer 52a before exiting the tissue and passing on to the detector 54. As the energy from the second layer 52b enters the first layer 52a it is selectively absorbed by the compounds present in the first layer 52a. This absorption is just like the absorption that takes place in the classical transmission cell spectroscopy apparatus. The first layer 52a absorbs the energy from the second layer 52b selectively—at specific wavelengths.

The total energy radiated from the subject appears very much like conventional black body emissions. However, if careful observation is made the difference between a black body emission spectra and the emissions after absorption by deeper layers when an internal temperature gradient exists, subtle but important differences can be observed. The model of FIG. 2 was implemented using typical numbers and produced the output shown in FIGS. 3a and 3b.

Figure 3A:
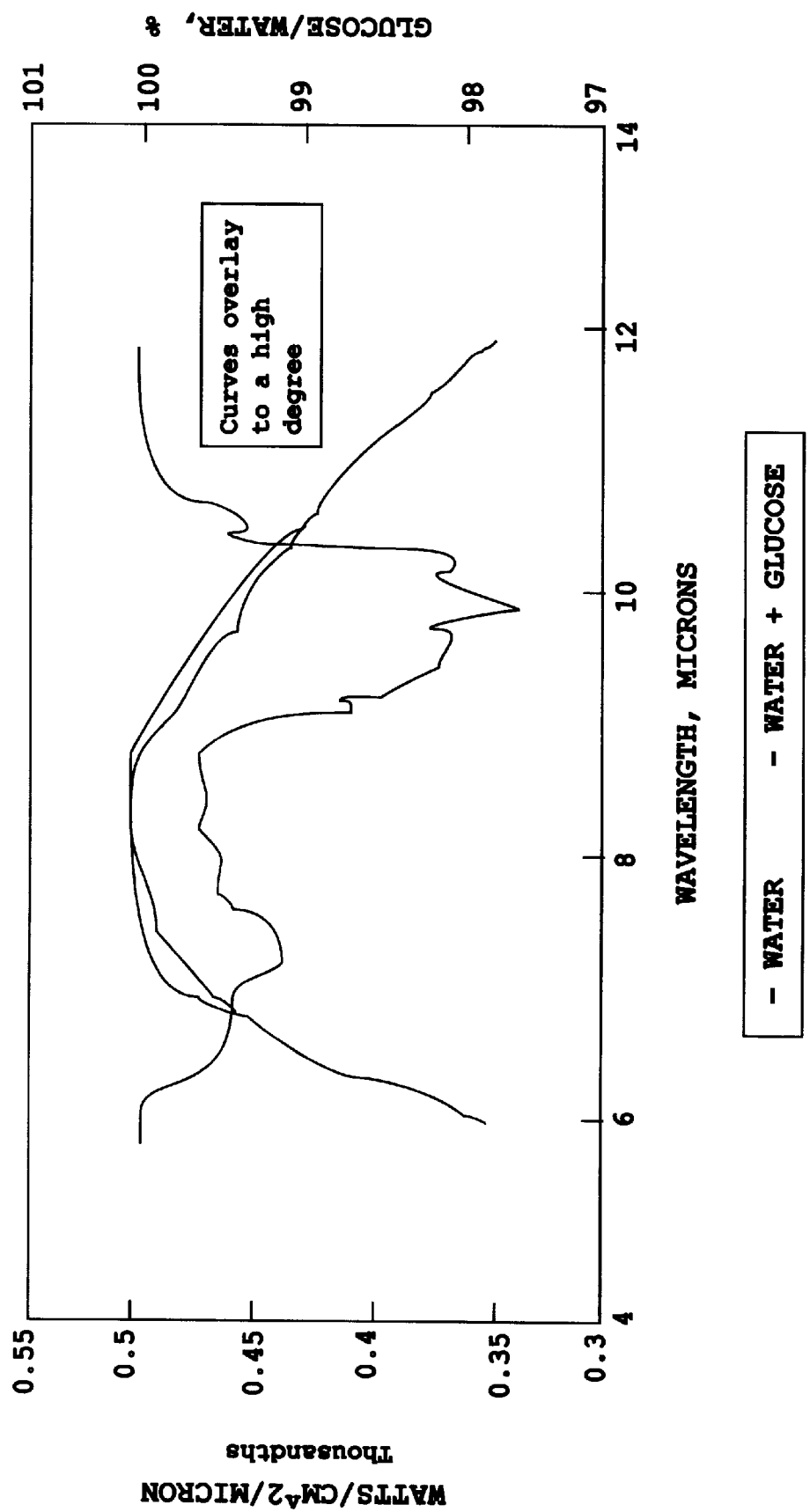
FIG. 3a is a diagram of an absorption spectrum of a constituent in a body, when the body has a thermal gradient.
Figure 3B:
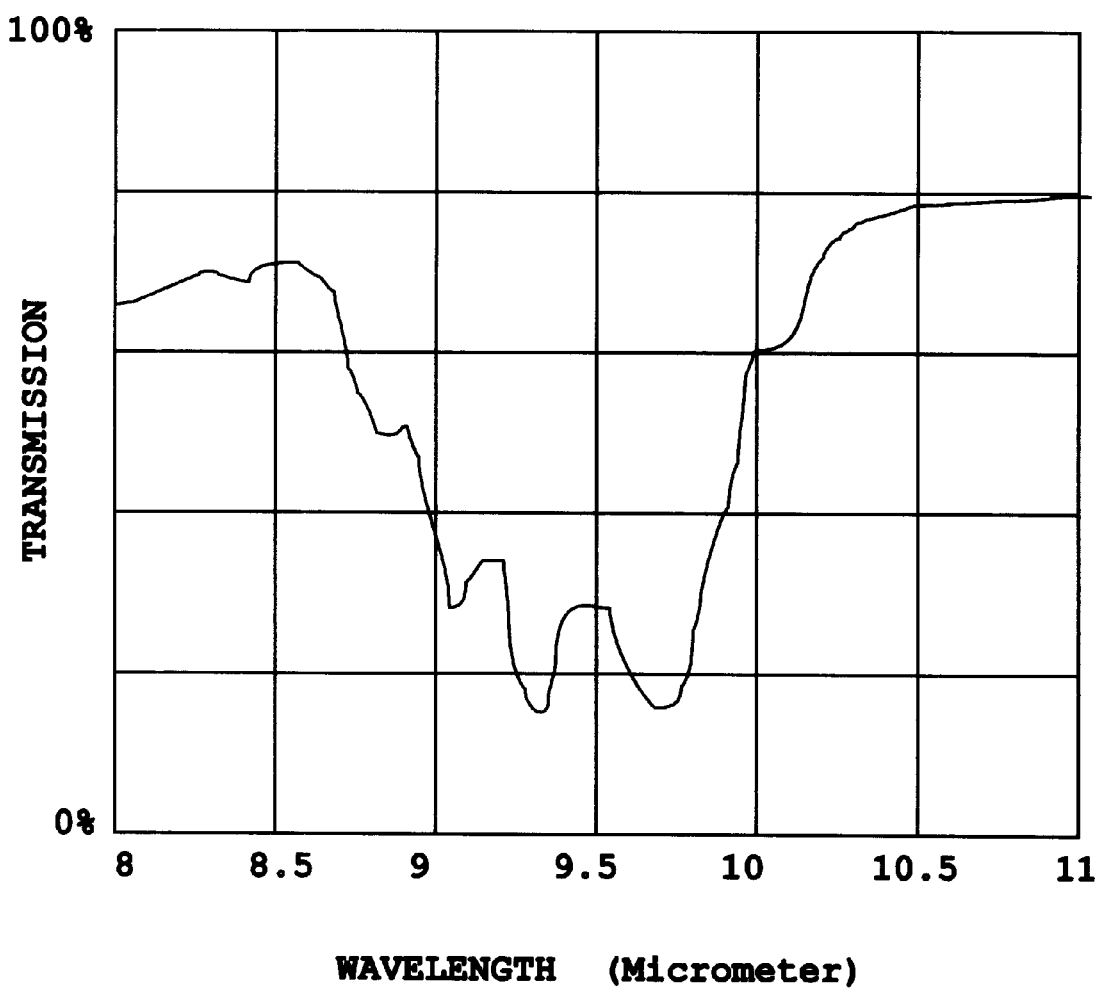
FIG. 3b is an absorption spectra of glucose produced using conventional transmission spectroscopy.

With this model, for illustrative purposes two spectra are shown FIG. 3a, one for water and one for water with glucose dissolved in it. In normal physiological concentrations of glucose both spectra would look very similar to the Planck emission curves describing a black body and would be nearly overlapping. However, with high concentrations of glucose in solution (5%) a small perturbation near 9 microns can be observed. When the ratio of the glucose solution to the pure water emission spectra are taken the characteristic glucose absorption spectra emerges. The magnitude of the spectra depends on the glucose concentration and the temperature gradient. The gradient induced glucose spectra compares favorably with the conventional transmission spectra of glucose shown in FIG. 3b.

In order to elucidate spectral absorption of constituents of bodies where the presence and concentration of the constituent varies by depth below the surface it is necessary to establish and control the magnitude, propagation velocity and contour profile of the thermal gradient described previously. The above-identified model addressed only the absorption of layers of homogeneous material subjected to a large steady state thermal gradient. One purpose of this invention is to dynamically establish and control the magnitude and propagation depth of a thermal gradient to elucidate selectively (as a function of time and depth) the thermal absorption of the deeper layers below the surface within which the concentration of the tissue constituent is of physiological interest.

Figure 4:
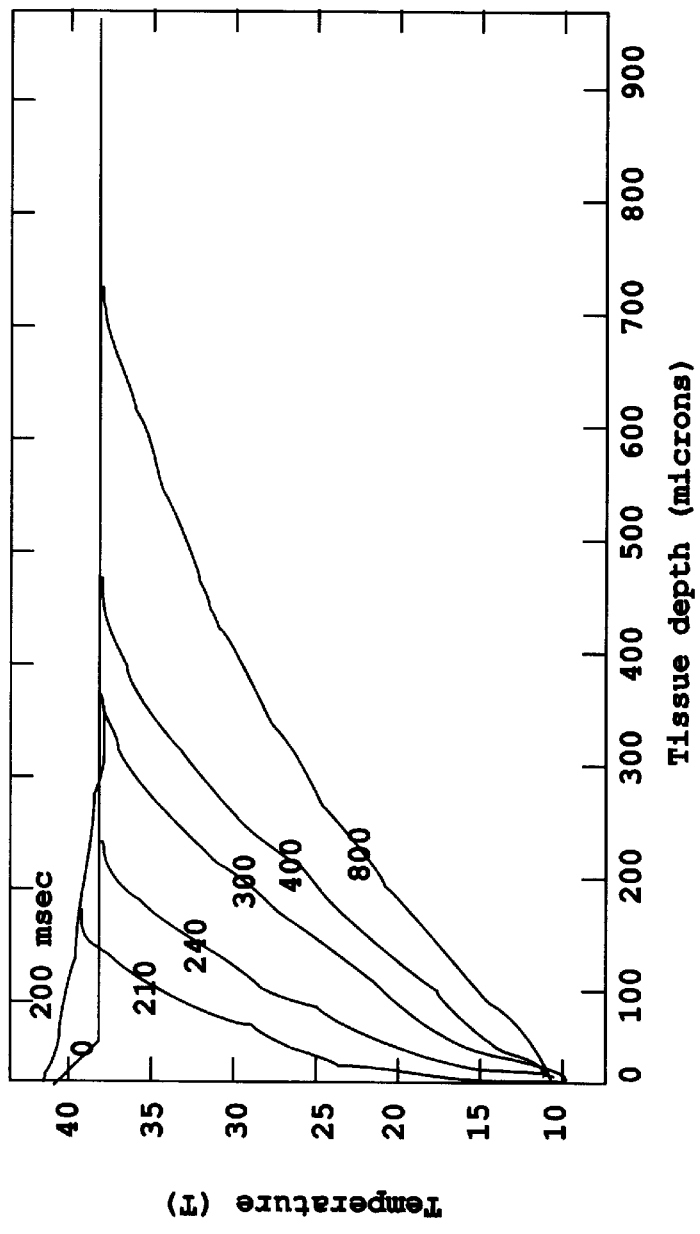
FIG. 4 is a curve that shows the influence of the gradient interacting with time/depth dependent constituents of interest.

The infrared spectral content of absorption by subsurface layers will be directly related to the magnitude of the gradient existing across the layer. The magnitude of the gradient will vary from near zero before the thermal gradient has propagated to that layer to a maximum value approximately defined by the difference between the high temperature within the body and the low temperature at the surface of the body divided by the thermal gradient depth. FIG. 4 also describes the three variables of the dynamics associated with the time dependency of establishment, propagation and thermal gradient contour profile induced into a body. FIG. 4 describes the influence of the gradient interacting with depth dependent concentrations of the constituents of interest, and FIG. 5 the corresponding infrared spectral absorption pattern. The thermal gradient contour profile is a three dimensional representation of the above concepts.

Figure 5:
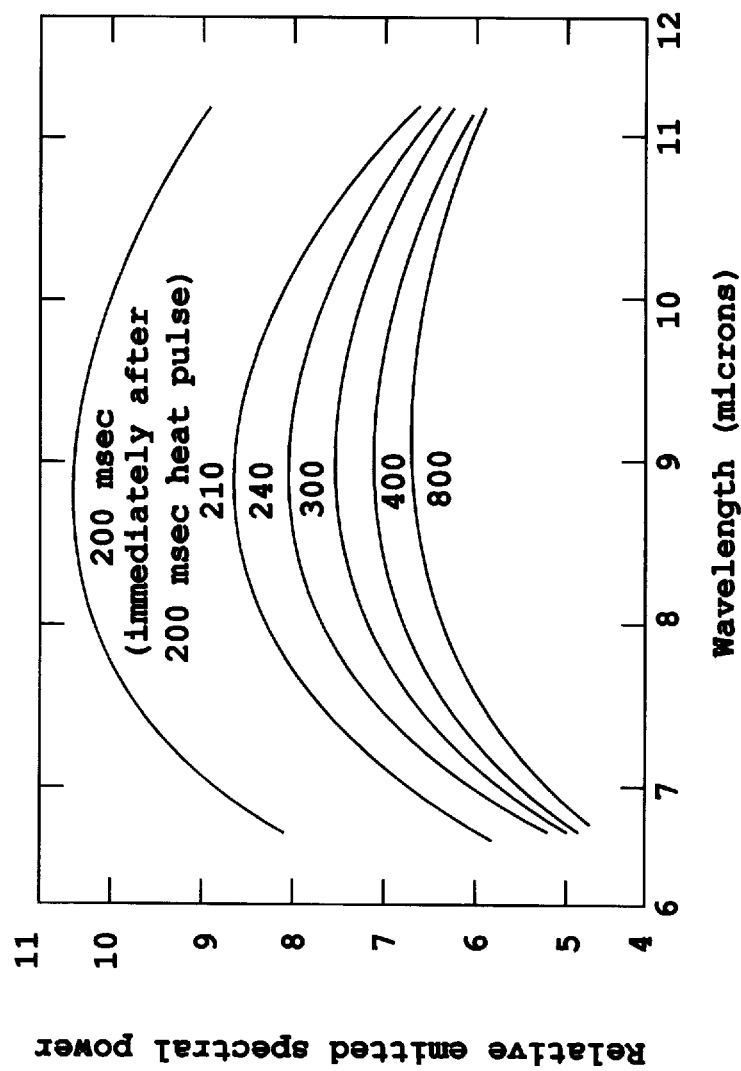
FIG. 5 is a curve which illustrates the time dependency of the spectral content of the absorption pattern.

The resultant time (depth) dependency of the spectral information, shown in FIG. 5, illustrates that in human tissue the spectral content of interest will not begin to appear in the infrared absorption until approximately 100 ms (milliseconds) after cooling the external surface has begun and will transiently increase in intensity with a maximum occurring between 125 to 175 ms. After which the spectral content will decrease until approximately 200 ms. The decrease is due to the accumulative effects of both optical absorption as a function of increasing depth and to the change in its profile (the decrease in the magnitude of the gradient).

In order to optimize the thermal gradient in magnitude, propagation velocity, and contour profile, the thermal boundary conditions and thermal conductive properties of the means for heating and cooling the body must be considered. The considerations are particularly important for physiological application of the invention wherein the body refers to the human body and avoidance of temporary or permanent damage to the tissue is paramount. The maximum temperature to which human tissue can be subjected for prolonged or repeated exposure is 41–42° C. The minimum temperature is less well defined but estimated at −3° C. for transient exposure of 1–2 seconds.

The mechanism or process for creating and controlling the magnitude, propagation velocity and contour profile of the thermal gradient incorporates cyclic cooling and re-warming of the observation site. The mechanism or process for cooling the surface of the tissue target site is unique in the present invention in that the cooling body becomes part of the optical pathway through which the infrared energy must pass in order to be recorded.

For comfort of the subject upon whom the measurement is being made, it has been determined that the surface areas being heated and cooled should be approximately equal in size and approximately ¾" in diameter. To improve the S/N in the measurement it is advisable to repeatedly observe the depth selective spectral emissions. The mechanical device designed to repetitively and repeatably cool and re-heat the target tissue area provides the capability to rapidly cycle between heating and cooling with a typical cycle time of 5 seconds.

Uniformity of the heating and cooling across the surface area of the target tissue and within the volume under the target site is also an important parameter for maximizing the spectral signal content of the depth dependent emissions. Reduced uniformity of the temperature across the surface during either heating or cooling will result in the thermal gradient profile not being uniform in a direction perpendicular to the surface. The resulting absorption spectra will contain absorption information from differing depths across the surface of the target thus loosing specificity between spectral content change and depth.

Quantifying the Amount of Constituent Present

Quantification of the substances of interest is derived from the relative energy emitted through a gradient enhancement technique. To quantify the amount of the substance of interest, a ratio method employs the relative energy emitted at a wavelength known to be absorbed by that substance normalized by the absorption at one or more reference wavelengths.

Figure 6:
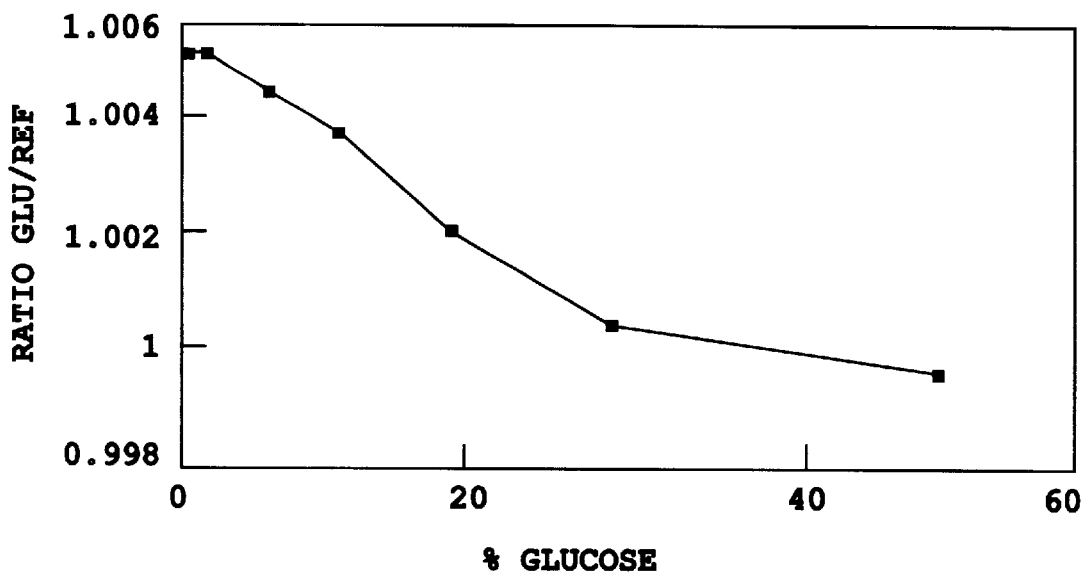
FIG. 6 contains two graphs showing the ratio of analytical band energy/reference band energy vs. Constituent concentration and the analytical and reference bands superimposed on the infrared energy spectra in accordance with FIG. 3.
Figure 6:
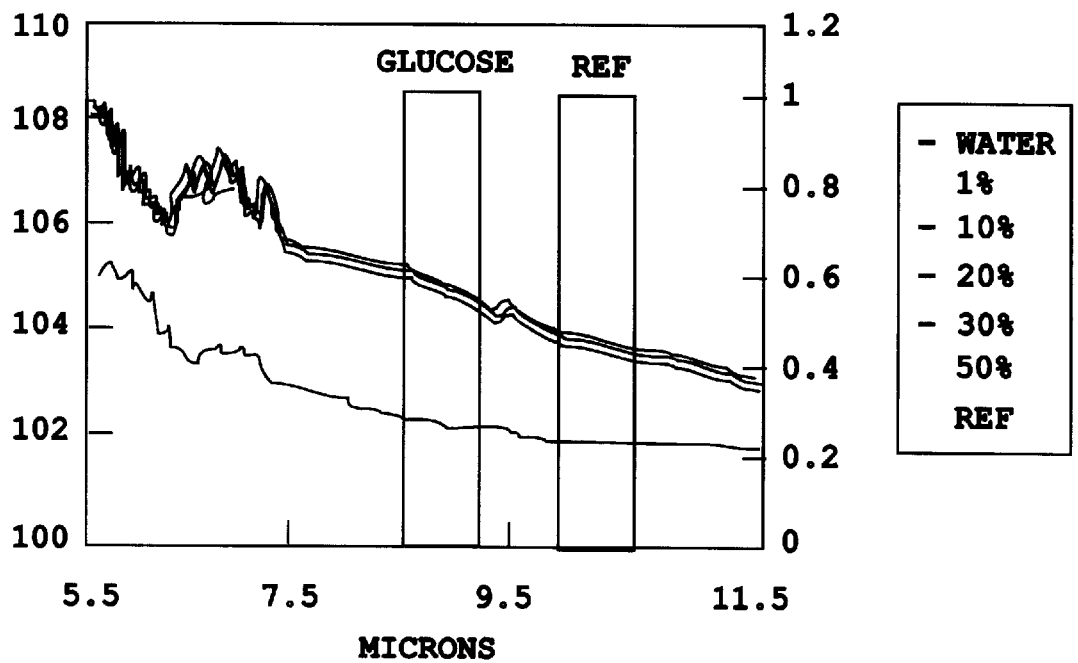

The ratio of analytical band energy/reference band energy is plotted vs. Constituent concentration in the curve shown in FIG. 6. The upper portion of this figure shows the relationship between the emitted energy ratios and the concentration of the analyte. The lower portion of the figure shows the emitted energy vs. wavelength for several concentrations of glucose and the glucose and reference analytical bands used. Those skilled in the art will recognize this relationship as Beer's Law.

$$I = Io * exp-x\ c\ a$$

Where:

I=energy detected

Io=energy emitted x=path length c=number of absorbing molecules a=absorption constant It is not necessary to explicitly measure x (path length) to use this technique to compute useful glucose concentrations. For example, metabolic glucose concentrations are expressed in mg/dL or milligrams of glucose per 100 milliliters of fluid. Thus, what is actually required is not an absolute measurement of glucose molecules but a ratio of glucose to other fluid molecules per unit volume.

The technique presented here can be used to measure water, proteins, and glucose. Examination of the absorption spectra reveal that water has characteristic absorption bands near 6.1 and 12 microns, proteins absorb from 6.0 to 8.4 microns and glucose absorbs from 8.5 to 10.0 microns. Using these absorption bands one can compute the relative concentration of each species by ratioing. The ratio of glucose to water yields a representation of glucose in mg/dl.

To more clearly understand the operation of the present invention in the context of a particular embodiment or embodiments, refer now to the following discussion.

In a first embodiment, a natural occurring thermal gradient like that described above in the context of a human body is utilized. That is, the temperature gradient is such that the temperature is cooler at a location within the body closer to the detector (i.e. the surface temperature of the skin is 30° C.) than at a more distant location (i.e. the interior skin layer 37° C.).

Figure 7:
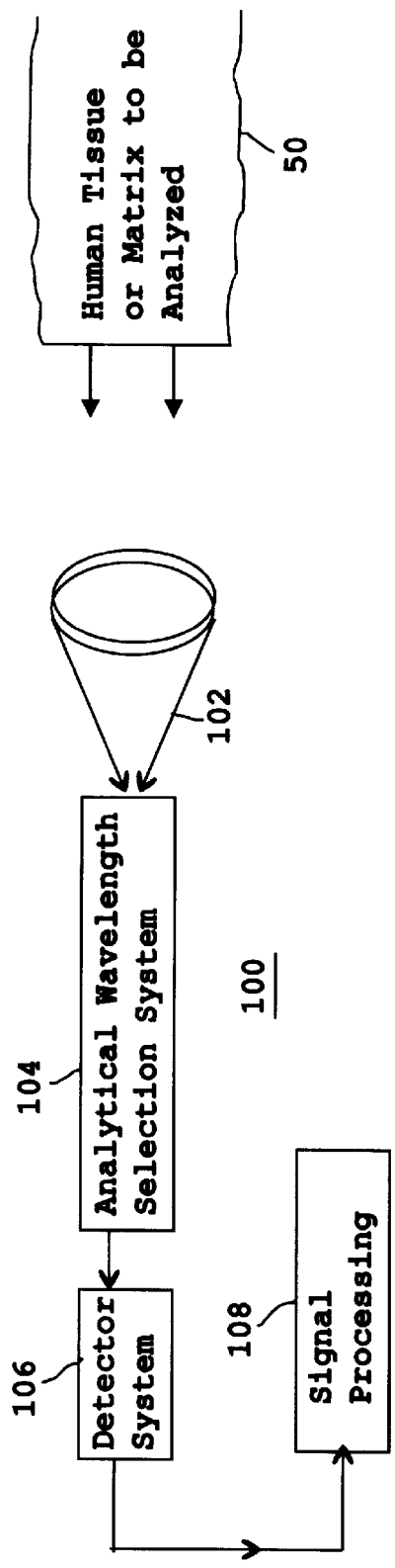
FIG. 7 is a first embodiment of a spectrometer in accordance with the present invention.

Referring now to FIG. 7, what is shown is a first embodiment of such a system 100. In this embodiment, infrared emissions from the body 50 are collected by an optical collector 102. A particular wavelength is selected that corresponds to a particular constituent in the body 50, by a wavelength selection system 104. A detector 106 receives information from the selection system 104. A signal processing system 108 processes the information. The various elements of the system will be described herein below.

Analytical Wavelength Selection System 104

Several means of selecting the analytical wavelengths can be used such as:
Discrete infrared bandpass filters
An interferometer
A spectrophotometer
A grating monochrometer
A variable filter monochrometer In the preferred embodiment a set of 9 discrete analytical filters manufactured by Optical Coating Laboratories Inc. (Santa Rosa, Calif.) are used. In an alternate embodiment a PERKIN ELMER (England) System 2000 Fourier Transform Infra Red Spectrophotometer (FTIR) is used in place of the filters. The filters provide a compact system that is rugged and relatively economical. The use of a specific set of bandpass filters restricts the instrument to analyzing only pre selected wavelengths. The use of the FTIR allows the optical measurements of all wavelengths. When using an FTIR the final analysis wavelengths are selected in the signal processing computer. Therefore an instrument built with discrete filters is dedicated to measuring a predetermined compound, e.g. glucose, while an instrument built using an FTIR can be directed via software modifications to measure any of a number of compounds such as glucose, alcohol, etc.

Detector System 106

The detector system converts the infrared energy into usable electrical signals. The detector system 106 typically comprises of two components, an infrared detector and a pre-amplifier.

In the preferred embodiment the detector is an array of 9 Photo Voltaic Mercury Cadmium Telluride (PVMCT) detectors. A detector such as a FERMIOINICS (Simi Valley, Calif.) model PV-9.1 with a PVA-481-1 pre-amplifier is acceptable. Similar units from other manufacturers such as GRASEBY (Tampa, Fla.) can be substituted.

Signal Processing System 108

The signal processing system 108 used in the preferred embodiment is a personal computer (PC) manufactured by Digital Equipment Corp. (DEC) model 4331px. Others can be substituted. The computer provides a computation engine, display and user interface to the system. An A/D converter system manufactured by Strawberry Tree, Inc. (STI) in San Jose, Calif., model "WORKMATE PC" is used to interface the analog signals from the detector to the computer.

In the alternate configuration using the FTIR the Perkin Elmer instrument incorporates a GRASEBY 1×1 MCT detector and includes a computer interface so the Fermionics and STI devices are not required to complete the system.

Figure 8:
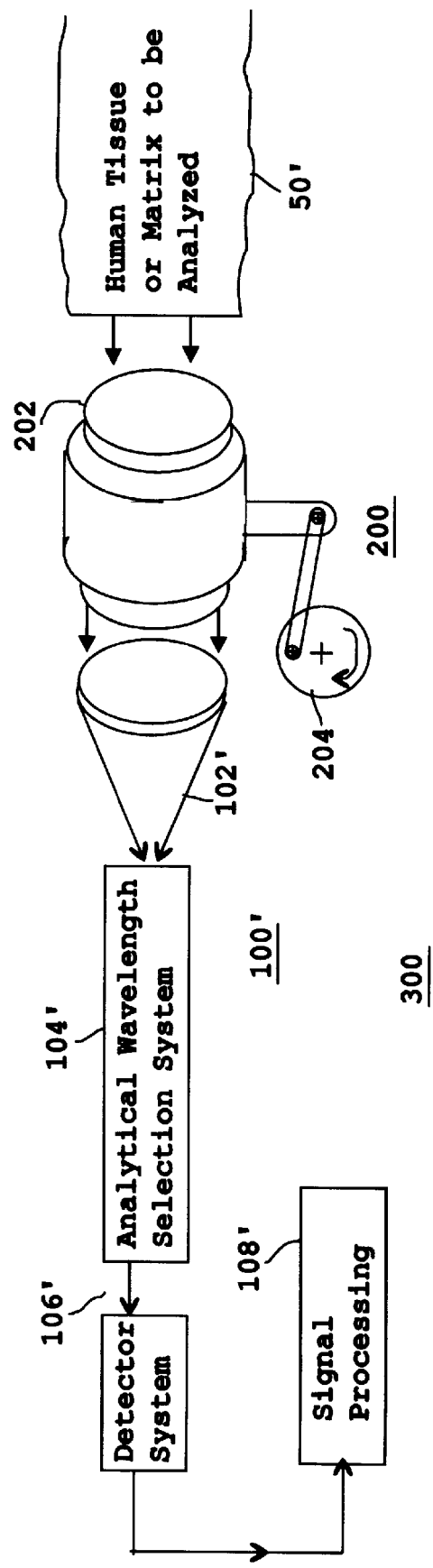
FIG. 8 is a second embodiment of spectrometer in accordance with the present invention.

Referring now to FIG. 8, what is shown is a general block diagram of a second embodiment of a system in which a temperature gradient is enhanced or induced in the body to clearly establish a temperature differential. The system 300 includes similar components to those shown in system 100 except system 300 includes a thermal gradient inducer 200 for inducing a temperature gradient within the body. The inducer 200 includes chilling mechanism 202, which repeatedly contacts the body 50' through a reciprocating mechanism 204.

In a preferred embodiment, the chilling mechanism 202 is brought in contact with a body. Also in a preferred embodiment, the chilling mechanism is a chilled germanium crystal. The germanium material allows the infrared energy to pass through the chilling mechanism and in to the optical collector while still contacting the body and enhancing the temperature gradient. Utilizing this system after each contact of the chilling mechanism with the body 50' an optical measurement is made by the system 100' and the measurements averaged over several contact cycles.

Chilling Mechanism 202

In a preferred embodiment the chilling mechanism 202 is a germanium crystal which is manufactured by Meller Optics of Providence, R.I. It is 0.75" diameter and 0.75" long. Both end surfaces are "polished to optically flat condition". Other materials, geometries and sizes are acceptable. The crystal's function is twofold. One is to cool the measurement "site", and the other is to efficiently collect and transmit the infrared energy to the collector and detector systems.

The germanium crystal is chilled by a water cooling jacket to approximately 10 Deg. C. This temperature provides an enhanced temperature gradient at the measurement site to enhance the infrared signal to allow detection by conventional detectors. The cooling jacket is typically a water jacket connected to a water bath such as a LAUDA model RM-20. The water bath is operated at 10° C. and the bath's internal circulating pump circulates water inside the jacket to cool the crystal. Alternately the crystal can be cooled with a thermo-electric cooler such as Mellcor (Trenton, N.J.) FCO.6 controlled by an Alpha Instruments (Johnston, R.I.) TEC controller. Additional means for cooling the target surface include cold N2 or other gases, infrared transmissive cooling fluids circulated immediately in contact with target window rear surface.

Since the temperature of the crystal surface is below the dew point special precautions must be taken to assure that no condensation exists on any surface through which infrared energy is collected. This necessitates either dehumidified enclosures, mechanical defrosting of the crystal surfaces or chemical means for dew prevention.

After the germanium crystal contacts the measurement site the proper gradients exist for approximately 500 ms. After that time the crystal is removed and the site re-warmed.

Reciprocating Mechanism 202

In a preferred embodiment, movement of the crystal is accomplished by a cam and lever mechanism driven by a gear head motor such as a MicroMo Inc. (St. Petersburg, Fla.) model 2842S. Other mechanisms could be substituted. The requirement is only that the crystal be moved ⅛" to ¼" away from the skin to allow re-warming.

Re-Warming can be accomplished passively by just letting the body re-warm itself by means of local blood flow to the measurement site. Initial body surface temperatures are typically 30° C. and after 500 ms of chilled crystal contact the skin surface cools to about 20° C. Natural re-warming will take approximately 15 seconds. Alternately the re-warming can be accelerated by blowing warm air at the measurement site or bringing the measurement site in contact with a warm conductive surface.

The surface or air temperature should not exceed 50° C. to avoid discomfort. Optical methods of re-warming by directing infrared, UV or visible light at the measurement site are also applicable. Alternate re-warming means may include ultrasound or microwave. Unlike the cooling means the re-warming mechanism of the present invention need not be infrared transmissive since no signals are measured during the re-warming phase of the cycle. The time of contact with or exposure to the re-warming source is determined by the time required to raise the temperature of the target site tissue from the cooled temperature, to approximately 41° C.

After the surface has been re-warmed to between 30 and 40° C. the measurement cycle can be repeated. In the preferred embodiment up to 100 cycles will be used to constitute a determination of blood glucose level.

When the crystal is in contact with the patient's skin infrared energy in the 3 to 15 micron band passes from the skin through the crystal and into the dispersive element of the system. The purpose of the dispersive element is to select analytical wavelengths. With the proper wavelengths selected the computation of glucose concentrations based on the theory described above can be accomplished. A typical operating sequence is shown below.

Operating Sequence

Step 1. Bring instrument in contact with patient's forearm.

Step 2. Reciprocating mechanism brings chilled crystal in contact with patient's skin for 500 ms Step 3. Optical energy is detected, selected, and analyzed by the system signal processor to determine glucose concentration per the algorithm discussed above.

Step 4. Reciprocating mechanism removes crystal from skin.

Step 5. Skin re-warms.

Step 6. After skin has re-warmed to approximately 30 to 40 Deg. C. the cycle is repeated until 100 separate glucose determinations have been made.

Step 7. Average all 100 measurements and report result.

The useful range of analytical wavelengths of the present invention is wide. In a sample at room temperature (25° C.) the peak energy emissions are at 9.8 microns. In the case of a human body (maintained typically at 37° C.) the peak emissions are near 9.3 microns. Substances at other temperatures have peak emissions at other wavelengths. In the case of room temperature or human body temperature samples the analytical range containing most of the energy is from 2 to 14 microns. Energy levels outside of that band are very low. To use the technique in shorter wavelength bands the sample can be heated.

Figure 9:
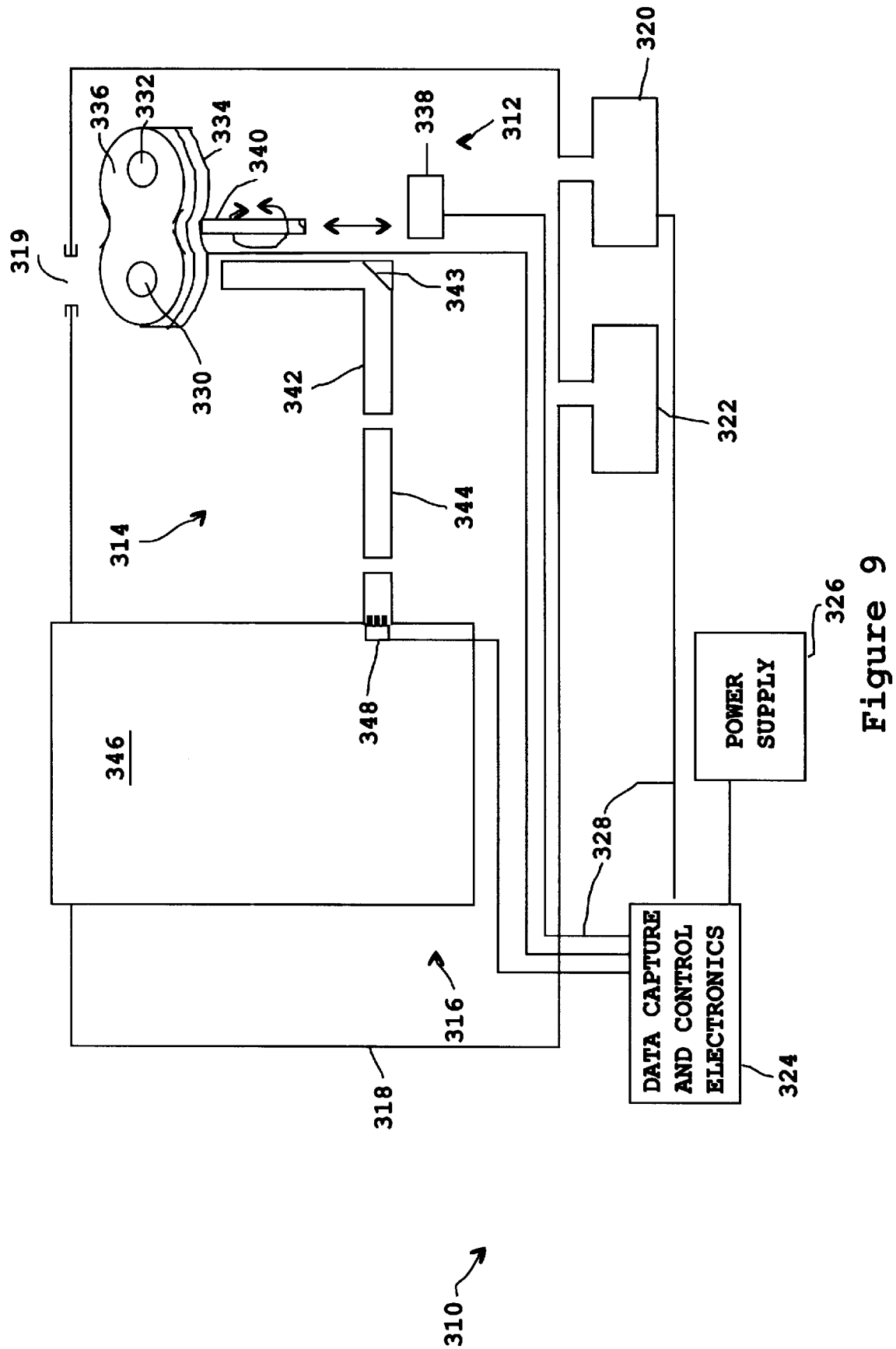
FIG. 9 is a third embodiment of a spectrometer in accordance with the present invention.

Another embodiment of a spectrometer according to the invention, generally indicated by the numeral 310, is illustrated in FIG. 9. The spectrometer 310 comprises a thermal gradient subsystem 312, an optics module 314, an infrared detector subsystem 316, all surrounded by an insulated housing 318. With the exception of an aperture 319, the housing 318 is substantially airtight.

In communication with the housing 318 is a vacuum source 320 and a dry gas source 322.

A data capture and control system 324 and a power supply 326 are coupled to various components of the spectrometer 310 by means of electrical signal and power lines 328.

The thermal gradient subsystem 312 includes two germanium crystals 330, 332. The two germanium crystals 330, 332 each provide a thermal mass which is used to transfer heat conductively to or from a patient's skin. In operation, the germanium crystal 330 is heated as described below, while the other germanium crystal 332 is cooled. To facilitate a better understanding of the invention therefor, these crystals will be referred to henceforth, for illustrative purposes only, as the warm germanium crystal 330 and the cold germanium crystal 332.

The warm and cold germanium crystals 330, 332, which are transmissive to infrared light, are mounted on a copper support 334, and are held in place by an aluminum bracket 336. The copper support 334 and the aluminum bracket 336 are both provided with apertures so that infrared light can pass unobstructed through the germanium crystals 330, 332.

The copper support 334 is coupled to a drive mechanism 338 by means of a shaft 340. The drive mechanism 338 is used to impart a reciprocating rotary motion to the copper support 334, whereby the germanium crystals 330, 332 are alternately positioned adjacent to the aperture 319. The drive mechanism 338 is also used to impart a reciprocating linear motion to the shaft 340, whereby the germanium crystal which is positioned adjacent to the aperture 319 can be advanced or retracted from the aperture 319.

A thermoelectric peltier device and a temperature sensor are placed between the copper support 334 and the aluminum bracket 336 adjacent to each of the warm and cold germanium crystals 330, 332. The warm germanium crystal 330 is heated by its thermoelectric device to approximately 48° C. and this temperature is maintained by conventional temperature control electronics. The cold germanium crystal 332 is cooled by its thermoelectric device to approximately 5 to 6° C., and this temperature is again maintained by conventional temperature control electronics.

Located below the thermal gradient subsystem 312 is the optics module 314. The optics module 314 consists of an infrared transmission path 342 and an homogenizer 344. Infrared light which has passed through either one of the germanium crystals 330, 332 is passed to the homogenizer 344 by means of the optical transmission path 342. The optical transmission path 342 is provided with a mirror 343 for reflecting the infrared light through a 90° angle.

The homogenizer 344 serves to unfocus the infrared light completely as it passes through the homogenizer 344. This ensures that the sensors in the infrared detector subsystem 316 are equally affected by any nonuniformities present in the infrared light before homogenization.

Infrared light leaving the homogenizer 344 enters the infrared detector subsystem 316. The infrared detector subsystem 316 comprises a dewar vessel 346 and an infrared detector array 348. The dewar vessel 346 is filled with liquid nitrogen to cool the infrared detector array 348.

The infrared detector array 348 comprises nine photovoltaic mercury cadmium telluride (MCT) infrared detectors arranged in a three by three configuration. Located in front of each of the nine infrared detectors in the detector array 348 is a single wavelength infrared filter. Each detector is therefore a sensor for one particular band of infrared energy, and the output of the nine infrared detectors together provides the desired infrared spectrum. In the illustrated embodiment of the invention, the nine sensors are respectively sensitive to infrared energy at 9.23, 10.7, 5.17, 12.0, 6.97, 10.27, 7.31, 6.03 and 8.4 micron wavelengths.

Each of these wavelengths is selected to provide particular information which is relevant to the determination of the composition of the human or animal tissue under analysis. For example, infrared light at the 5.17 micron wavelength transmits well through water. Accordingly, it can be assumed that infrared light at this wavelength comes from deeper within the tissue than the shallow volume through which the induced temperature gradient is propagating, and is thus an indication of the internal temperature of the tissue. For the purposes of subsequent processing of the infrared spectrum measured by the spectrometer 310, it can then be assumed that a black body at this observed temperature is located behind the volume through which the temperature gradient is propagating.

On the other hand, water absorbs infrared energy very well at the 6.03 micron wavelength. Accordingly, almost all infrared energy at this wavelength which originates deeper in the tissue will be self absorbed by the tissue before it reaches the skin surface. Therefor, almost all of the energy at this wavelength originates at the skin surface, and can be used as an indication of the skin surface temperature.

In the measurement of the glucose content in the tissue, the 9.23 micron wavelength is particularly important, as infrared energy is absorbed by glucose at this wavelength. In particular, the amount of the infrared energy absorbed at this wavelength depends on the glucose concentration in the body, and the signal from this detector can thus subsequently be processed in accordance with the principles of transmission spectroscopy theory to yield a value for the glucose content in the body.

The infrared energy at other wavelengths provides further information on the composition of the body under test. For example, the infrared energy at the 10.7 micron wavelength is substantially unaffected by the composition of a human or animal body, and it can thus be used as a reference. The amount of infrared energy detected by the remaining sensors is dependent on the amount of various proteins in the body. These proteins may interfere with the infrared energy at the 9.2 micron glucose sensitive wavelength. Accordingly, the infrared energy levels at these wavelengths are quantified, so that the effects of such proteins can be removed in the subsequent processing.

Figure 10:
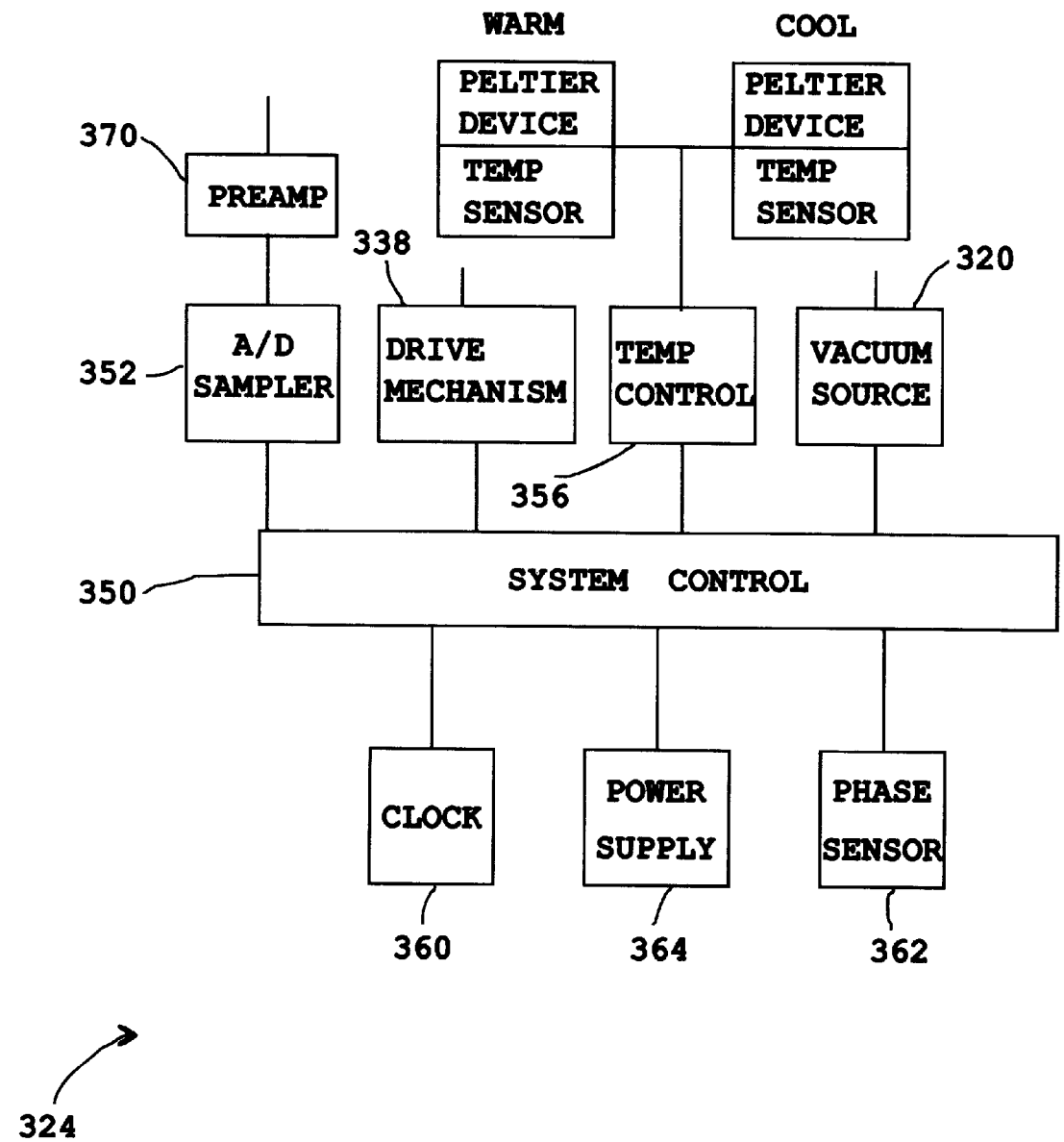
FIG. 10 is a schematic representation of the data capture and control electronics of the spectrometer illustrated in FIG. 9.

Referring now to FIG. 10, the data capture and control system 324 can be broken down into a number of functional elements, including an overall system control 350, an analog to digital (A/D) sampler 352, a drive mechanism actuator 354, a temperature control 356, a vacuum source actuator 358, a clock circuit 360 and an AC power line phase sensor 362.

The data capture and control system 324 receives power from a power supply 364, which in this embodiment of the invention is in the form of a battery, to improve isolation of the spectrometer 310 from AC power frequency interference.

The output signals from the detector array 48 are small, and are passed to a preamplifier 370. The preamplifier 370 boosts the magnitude of the signals before the signals are sampled by the A/D sampler 352. This sampling is done at an appropriate time as determined by the system control 350, and as discussed in more detail below.

Similarly, the system control 350 operates the drive mechanism 38 at predetermined times in the spectrometer operating sequence to advance, retract and rotate the shaft 340, the vacuum source actuator 358 operates the vacuum source 320 at predetermined times to create a partial vacuum in the area between the warm and cold germanium crystals 330, 332 and the aperture 319, while the temperature control 356 is used to operate the thermoelectric devices to maintain the desired temperature of the warm and cold germanium crystals 330, 332.

The system control 350 receives input from a clock circuit 360 for use in timing and synchronizing the various steps that take place in operation of the spectrometer 310.

The power line phase sensor 362 is used to sense the phase of AC power line interference. Output from the phase sensor 362 is used by the system control 350 as a trigger for various steps in the operation of the spectrometer 310, as described in more detail below. By synchronizing the operation of the spectrometer to the phase of power line interference in this way, the effect of such interference on the output of the spectrometer is reduced.

In use, the spectrometer 310 is powered up and an appropriate time interval is allowed to pass in order to allow the various subsystems to stabilize. In particular, the warm and cold germanium crystals must be permitted to reach their respective stable operating temperatures.

During operation of the spectrometer 310, dry gas is continuously supplied to the interior of the housing 318 from the dry gas source 322. This ensures that substantially no moisture condenses on the cold germanium crystal 332, which is generally at a temperature below the dew point of the air surrounding the spectrometer 310. This is important because the presence of water on the cold germanium crystal 332 would interfere with the infrared emissions received by the spectrometer 310, causing inaccuracies in the data collected by the spectrometer.

After the spectrometer has reached a stable operating condition, a patient puts an arm or other body part over the aperture 319. A measuring cycle is then actuated by an operator, and the warm germanium crystal, at a temperature of approximately 48° C. is positioned adjacent to the aperture 319 in close proximity to the patient's arm (approximately 3 mm.). This is accomplished by appropriate rotation and translations of the shaft 340 by the drive mechanism 338, under control of the system control 350.

After a pause of approximately a second to allow the temperature of the warm germanium crystal 330 to stabilize again, the system control 350 actuates the vacuum source 320, which reduces the pressure in the space between the warm germanium crystal 330 and the aperture 319 by approximately 5" Hg below ambient atmospheric pressure. This draws the portion of the patient's arm covering the aperture into intimate contact with the warm germanium crystal 330, thereby to preheat the patient's epidermal layer conductively.

After the warm germanium crystal 330 has been in contact with the patient's arm for two seconds, the system control 350 deactivates the vacuum source 320 and withdraws the warm germanium crystal 330 from the aperture 19. The shaft 340 is rotated through 180° and the cold germanium crystal 332 is advanced into close proximity to the patient's arm.

After a pause of approximately a second to allow the temperature of the cold germanium crystal 332 to stabilize, the system control 350 actuates the vacuum source 320 to draw the portion of the patient's arm covering the aperture into intimate contact with the cold germanium crystal 330 as described above.

The contact between the cold germanium crystal 332 and the skin of the patient transfers heat conductively from the patient's skin to the cold crystal 332. This generates a temperature differential between the skin and the interior of the patient, and over the course of the measurement cycle, this temperature differential propagates into the patient's arm in the form of a "cold wave" as illustrated in FIG. 4. As the "cold wave" propagates into the patient's arm, the infrared emissions from the arm vary as described previously.

The infrared emissions from the arm pass from the aperture 319 through the cold germanium crystal 332, through the infrared transmission path 342, and into the homogenizer 344.

In the homogenizer 344, the infrared emissions are scrambled or unfocused, so that all of the sensors in the infrared detector array 348 are equally affected by any nonuniformities in the infrared emissions. Nonuniformities may be created in the infrared emissions by, for example, a blemish on the patient's skin. By providing the homogenizer 344, each sensor in the detector array 348 receives an equal signal from all parts of the patient's skin.

Upon exiting the homogenizer 344, the infrared emissions pass through the respective single wavelength infrared filters positioned in front of each of the nine sensors in the infrared detector array 348. Accordingly, each sensor generates a signal which is proportional to the infrared energy at a characteristic wavelength, which is then passed to the preamplifier 370.

The preamplifier 370 amplifies the signals received from the sensors in the detector array. The signals are then passed to the A/D sampler 352.

The A/D sampler 352, which was activated by the system control 350 as the patients's skin was drawn against the cold germanium crystal 332, samples the signals received from the preamplifier 370 at between 1 and 20 ms intervals as the cold wave propagates into the patient's epidermal layer.

While this sampling is taking place, the temperature control 356 is deactivated. If this was not done, the temperature control 356 could supply power unpredictably to the thermoelectric device mounted adjacent to the cold germanium crystal 332. This would result in an undesirable shift in the infrared background as sensed by the infrared detector array 348, which would in turn affect the accuracy of the data gathered by the spectrometer 310.

The initial actuation of the vacuum source 320 and the A/D sampler 352 is synchronized to a particular phase of the surrounding power line interference by the system control 350, as sensed by the 60 Hz power line phase sensor 362. By synchronizing the commencement of the measurement cycle of the spectrometer in this manner, the effect of power line interference is felt substantially equally in every measurement cycle. Due to the comparative nature of the processing of the data gathered by the spectrometer, this synchronization technique improves the accuracy of the data captured by the spectrometer.

After a two second measurement cycle, the vacuum source 320 is deactivated and the cold germanium crystal 332 is withdrawn from the patient's arm. At the same time, the A/D sampler 352 ceases sampling the signals received from the infrared detector array, and the temperature control 356 is reactivated.

The warm germanium crystal 332 is then again brought into position in close proximity to the patient's arm by the drive mechanism 338, under control of the system control 350 and drive mechanism actuator 354. At this stage, the spectrometer has completed a cycle of operation, and the warm germanium crystal 330 is positioned for a new cycle which will proceed as described above.

To ensure the accuracy and repeatability of the results, and to minimize the effects of any external interference, the cycle described above can be repeated as many times as desired to provide an average output from each of the infrared sensors in the infrared detector array 348. In the preferred mode of operation, the spectrometer undergoes thirty complete cycles, for a total operating time of five minutes per complete measurement.

For the spectrometer illustrates in FIG. 9, the system control 350 is a Dell XPS personal computer which has an inbuilt clock 360, a monitor for the display of the captured data, a keyboard, and a disk drive for storing the captured data. The A/D sampler 352 is an Intelligent Instrumentation PCI system, the power supply is a battery pack from SRS, the temperature control 356 is a CAL 3200, and the vacuum source 320 is a vacuum pump by GAST.

As far as the remainder of the spectrometer 310 is concerned, the dry gas source 322 is a supply of pure nitrogen, the drive mechanism 338 comprises one stepper motor for advancing and retracting the shaft 340, and one stepper motor for rotating the shaft 340.

The homogenizer is a 4" by 1.5" by 1.5" square tube with the inside walls plated with gold. The inside walls of the tube are highly polished and are therefor highly reflective to the infrared light passing through the homogenizer.

The sensors in the infrared detector array are photovoltaic MCT infrared detectors supplied by Fermionics, Inc.

Figure 11:
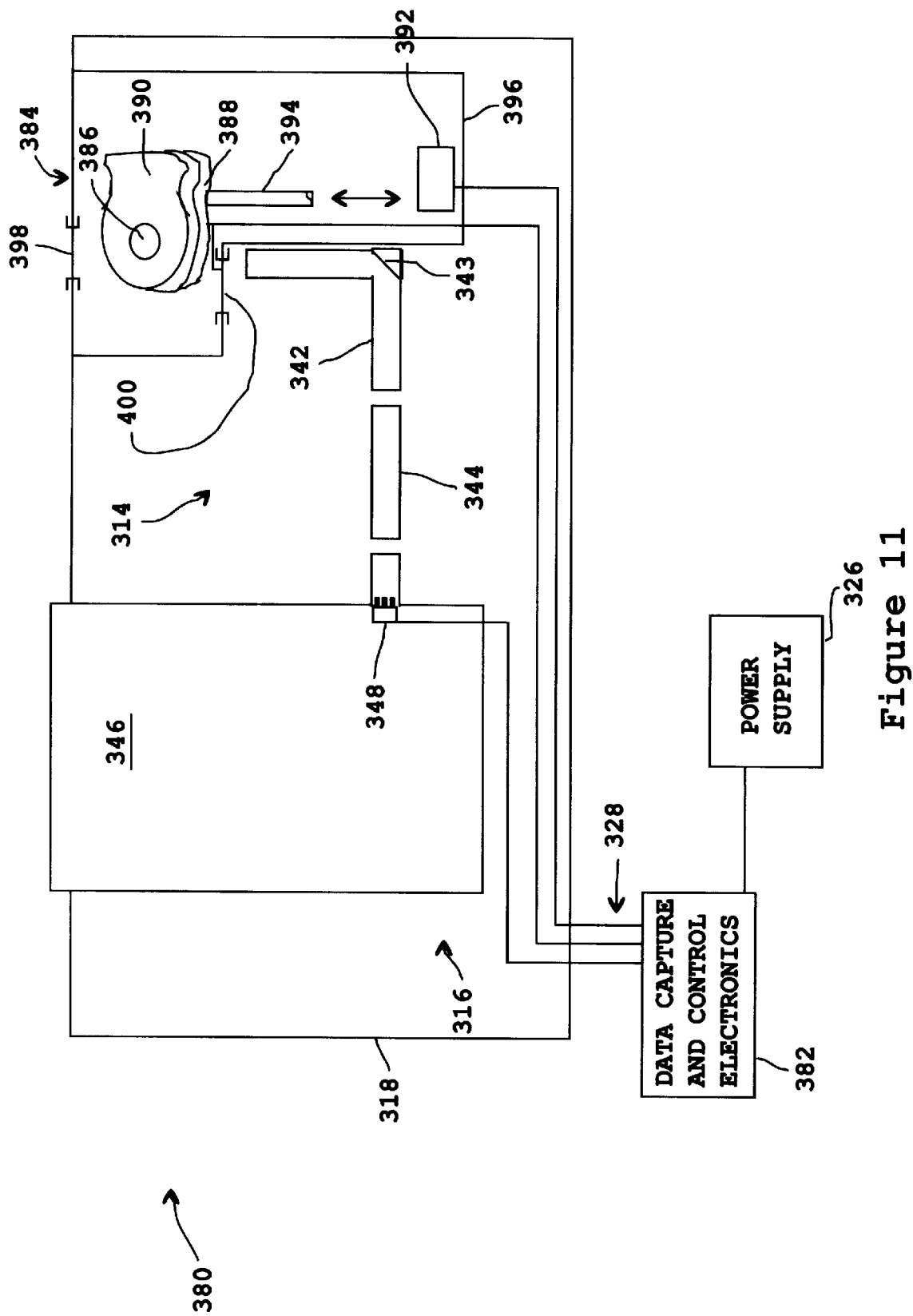
FIG. 11 is a fourth, and the best mode, embodiment of a spectrometer in accordance with the present invention.

The best mode embodiment of the spectrometer according to the invention, generally indicated by the numeral 380, is illustrated in FIG. 11. Many of the subsystems of the spectrometer 380 are identical to the subsystems described with reference to the spectrometer 310 illustrated in FIG. 9, and for purposes of conciseness, the descriptions of these subsystems will not be repeated here. In particular, the optics module 314 and the infrared detector system 316 are unchanged from the FIG. 9 embodiment.

The data capture and control system 382 in the FIG. 11 embodiment is almost identical to the data capture and control system 324 illustrated in FIG. 10, except that the vacuum source actuator 358 is no longer required.

The main differences between the spectrometers illustrated in FIGS. 9 and 11 are in the thermal gradient subsystem.

The thermal gradient subsystem 384 illustrated in FIG. 11 includes a cold germanium crystal 386. The cold germanium crystal 386 is mounted on a copper support 388, and is held in place by an aluminum bracket 390. The copper support 334 and the aluminum bracket 336 are both provided with an aperture so that infrared light can pass unobstructed through the cold germanium crystal 386.

The copper support 388 is coupled to a drive mechanism 392 by means of a shaft 394. The drive mechanism 338 is used to impart a reciprocating linear motion to the shaft 340, and hence to the cold germanium crystal 386.

A thermoelectric peltier device and a temperature sensor are placed between the copper support 388 and the aluminum bracket 390 adjacent to the cold germanium crystal 386. The cold germanium crystal 386 is cooled by the thermoelectric device to approximately −10° C., and this temperature is again maintained by the temperature control 356 of the data capture and control electronics 382.

The thermal gradient subsystem 384 is contained within an airtight enclosure 396. The enclosure 396 is filled with pure nitrogen gas to prevent water from condensing on the cold germanium crystal 386. As the thermal gradient subsystem 384 is sealed in this manner, the dry air source 322 of the FIG. 9 spectrometer can be eliminated.

The enclosure 396 is provided with two germanium windows 398, 400 located on either side of the cold germanium crystal 386. The germanium windows 398, 400 are both transmissive to infrared light, and are 1" in diameter and 0.015" thick. Each germanium window has a resistance heater mounted around its perimeter, and a temperature sensor. The germanium window 398 is heated to approximately 44° C., while the temperature of the germanium window 400 is maintained at ambient temperature. These temperatures are maintained by the respective resistance heaters under control of the temperature control of the data capture and control electronics 382.

By providing the sealed enclosure 384 which is filled with a dry gas, and by heating the two germanium windows 398, 400, the amount of condensation which occurs on the surfaces making up the infrared transmission path through the thermal gradient subsystem 384, is reduced. This reduces the variation in the readings obtained by the spectrometer 380.

The operating sequence for the spectrometer 380 is as follows:

The spectrometer 380 is powered up and an appropriate time interval is allowed to pass to in order to allow the various subsystems to stabilize. In particular, the cold germanium crystal 386 and the germanium windows 398, 400 must be permitted to reach their respective stable operating temperatures.

After the spectrometer has reached a stable operating condition, a patient puts an arm or other body part over the germanium window 398, and a measuring cycle is actuated by an operator. After approximately 90 seconds have passed, in which the germanium window 398 preheats the patient's epidermal layer, the system control actuates the drive mechanism 392 to advance the cold germanium crystal 386 into intimate contact with the germanium window 398, while at the same time disabling the temperature controls for the germanium windows 398, 400 and the cold germanium crystal 386.

The contact between the cold germanium crystal 386, which has a relatively large thermal capacity, and the germanium window 398, which has a relatively small thermal capacity, cools the germanium window 398 rapidly. The germanium window 398 in turn cools the skin surface of the patient, which generates a temperature differential between the skin and the interior of the patient. Over the course of the measurement cycle, this temperature differential propagates into the patient's arm in the form of a "cold wave" as before, and the infrared emissions from the arm vary as described previously.

It will be appreciated that, while the cold germanium crystal 386 is not brought directly into contact with the patient's skin as in the FIG. 9 embodiment, heat is still transferred conductively between the cold germanium crystal 386 and the patient's skin via the thin germanium window 398.

The infrared emissions from the patient's arm pass through the germanium window 398, through the cold germanium crystal 386, and out of the thermal gradient subsystem 384 through the germanium window 400.

The infrared emissions then enter the optical transmission path 342, and the sampling of the infrared emissions proceeds as described above with reference to the FIG. 9 spectrometer.

The movement of the cold germanium crystal 386 into contact with the germanium window 398 is synchronized to a particular phase of the surrounding power line interference by the system control 350, as sensed by the 60 Hz power line phase sensor 362.

Currently, for purposes of stability, the cold germanium crystal 386 is held in contact with the germanium window 398 for 15 seconds. As the actual propagation of the cold wave into the patient takes place in less than a second, it will be appreciated that, depending on the particular requirements of the measurements to be made, the contact time may be varied as desired.

After the outputs from the infrared detector array have been sampled and the data captured by the data capture and control electronics, the cold germanium crystal 386 is withdrawn from the germanium window 398 to a distance of approximately 0.1". Upon withdrawal of the cold germanium crystal 386, the temperature control for the cold germanium crystal 386 and the germanium windows 398, 400 is reactivated.

With the reestablishment of temperature control, the germanium window 398 is returned to its set temperature by its resistance heater. This in turn preheats the patient's skin in readiness for the next measurement cycle.

The total elapsed time from when the cold germanium crystal 386 is withdrawn from the germanium window 398, until the cold germanium crystal 386 is advanced again into contact with the germanium window 398, at the start of the next measurement cycle, is approximately 90 seconds. It will again be appreciated that, depending on the particular requirements of the measurements to be made, this time may be varied as desired.

At this stage, the spectrometer 380 has completed a cycle of operation, and a new cycle will proceed as described above.

As with the FIG. 9. spectrometer, to ensure the accuracy and repeatability of the results, and to minimize the effects of any external interference, the cycle described above can be repeated as many times as desired to provide an average output from each of the infrared sensors in the infrared detector array 348. In the preferred mode of operation, the spectrometer undergoes ten complete cycles, for a total operating time of ten minutes per complete measurement.

After the measurement cycles have been completed by either one of the spectrometers 310, 380, the data are processed as described in Applicant's patent application entitled "SUBSURFACE THERMAL GRADIENT SPECTROMETRY" filed on the same day as the application for this patent, under LaRiviere, Grubman & Payne Docket No. P698, the disclosure of which is incorporated herein by reference.

It will be appreciated that many modifications can be made to the spectrometers described above without departing from the spirit and scope of the invention.

For example, the three by three detector array 348 may be replaced by a single infrared sensor behind a variable filter wheel. The filter wheel will then rotate to provide the desired bands of infrared light to the single infrared sensor. In such a case, it will not be necessary to provide a homogenizer to equalize the infrared light between a number of infrared detectors in an array.

Also, room temperature infrared sensors may be used instead of sensors requiring cryogenic cooling. In such a case, the dewar vessel 346 will of course not be required.

Further, it will also be appreciated that energy at more or less than nine infrared wavelengths may be sensed to provide more or less information on the infrared spectrum emitted from the tissue. Generally, there is a tradeoff here between cost and accuracy, with more sensors/wavelengths sensed providing a better tolerance of extraneous factors and a more accurate final output. In a low cost production version therefor, where less accuracy may be acceptable, fewer sensors may be used.

Similarly, in a production version of the spectrometer, it may not be necessary to provide a preamplifier to boost the output signals.

Finally, it will be appreciated that meaningful data is obtained in a single application of the cold germanium crystal to the patient's skin. Accordingly, depending on the accuracy of the entire system, and the accuracy required of the final output, the spectrometer may not require a warm germanium crystal or window to preheat and reheat the patient's skin.

What is claimed is:

1. A spectrometer for the non-invasive generation and capture of thermal gradient spectra from living tissue, comprising:

a solid infrared transmissive thermal mass for inducing a transient temperature gradient in the tissue by means of conductive heat transfer with the tissue;

cooling means in operative combination with the solid infrared transmissive thermal mass for cooling the solid infrared transmissive thermal mass;

infrared sensor means for detecting infrared emissions emanating from the tissue as the transient temperature gradient progresses into the tissue in use, and for providing output signals proportional to the detected infrared emissions; and data capture means for sampling the output signals provided by the infrared sensor means as the transient temperature gradient progresses into the tissue.

2. A spectrometer according to claim 1 further comprising:

means for moving the solid infrared transmissive thermal mass relative to the tissue to bring the solid infrared transmissive thermal mass into a conductive heat transfer relationship with the tissue.

3. A spectrometer according to claim 2 wherein the means for moving the solid infrared transmissive thermal mass relative to the tissue comprises:

a housing in which the solid infrared transmissive thermal mass is contained, the housing defining an aperture therein over which the tissue can be placed; and means for reducing the gas pressure in area between the tissue and the solid infrared transmissive thermal mass to draw the tissue into direct contact with the solid infrared transmissive thermal mass.

4. A spectrometer according to claim 3 wherein the means for moving the solid infrared transmissive thermal mass relative to the tissue further comprises:

linear actuating means coupled to the housing and to the solid infrared transmissive thermal mass, the linear actuating means being operable to advance and retract the solid infrared transmissive thermal mass relative to the aperture.

5. A spectrometer according to claim 3 wherein the means for moving the solid infrared transmissive thermal mass relative to the tissue further comprises:

rotary actuating means coupled to the housing and to the solid infrared transmissive thermal mass, the rotary actuating means being operable to rotate the solid infrared transmissive thermal mass between a position in which the solid infrared transmissive thermal mass is adjacent to the aperture and a position in which the solid infrared transmissive thermal mass is remote from the aperture.

6. A spectrometer according to claim 5 further comprising:

an additional thermal mass coupled to the rotary actuating means, the additional thermal mass for heating the tissue; and heating means in operative combination with the additional thermal mass for heating the additional thermal mass, the rotary actuating means being operable to rotate the additional thermal mass between a position in which the additional thermal mass is adjacent to the aperture and a position in which the additional thermal mass is remote from the aperture.

7. A spectrometer according to claim 6 wherein the infrared sensor means comprises a single infrared detector positioned behind a rotatable variable filter wheel.

8. A spectrometer according to claim 3 further comprising a gas source in communication with the housing for supplying the interior of the housing with dry gas.

9. A spectrometer according to claim 1 further comprising:

homogenizing means through which the infrared emissions pass before being detected by the infrared sensor means, the homogenizing means for unfocusing the infrared emissions as they pass through the homogenizing means.

10. A spectrometer according to claim 9 wherein the homogenizing means comprises a tube having a reflective interior.

11. A spectrometer according to claim 9 wherein the infrared sensor means comprises an array of infrared detectors, each infrared detector in the array being positioned behind a single wavelength infrared filter thereby to make each infrared detector sensitive to a particular band of infrared energy.

12. A spectrometer according to claim 1 wherein the data capture means further comprises data capture and control means including a power line phase sensor for synchronizing the operation of the spectrometer to the phase of power line interference.

13. A spectrometer according to claim 1 further comprising:

an airtight enclosure in which the solid infrared transmissive thermal mass is contained, the enclosure including an infrared transmissive window over which the tissue can be placed; and means for moving the solid infrared transmissive thermal mass into contact with the window thereby to transfer heat from the tissue to the solid infrared transmissive thermal mass.

14. A spectrometer according to claim 13 wherein the means for moving the solid infrared transmissive thermal mass into contact with the window comprises:

linear actuating means coupled to the enclosure and to the solid infrared transmissive thermal mass, the linear actuating means being operable to advance and retract the solid infrared transmissive thermal mass relative to the window.

15. A spectrometer according to claim 14 further comprising:

heating means in operative combination with the window, for heating the window.

16. A spectrometer according to claim 15 wherein the enclosure is filled with dry gas.

17. A spectrometer according to claim 15 further comprising:

homogenizing means through which the infrared emissions pass before being detected by the infrared sensor means, the homogenizing means for unfocusing the infrared emissions as they pass through the homogenizing means.

18. A spectrometer according to claim 17 wherein the homogenizing means comprises a tube having a reflective interior.

19. A spectrometer according to claim 15 wherein the infrared sensor means comprises an array of infrared detectors, each infrared detector in the array being positioned behind a single wavelength infrared filter thereby to make each infrared detector sensitive to a particular band of infrared energy.

20. A spectrometer according to claim 15 wherein the infrared sensor means comprises a single infrared detector being positioned behind a rotatable variable filter wheel.

21. A spectrometer according to claim 13 wherein the data capture means further comprises data capture and control means including a power line phase sensor for synchronizing the operation of the spectrometer to the phase of power line interference.

22. A spectrometer for the non-invasive generation and capture of thermal gradient spectra from living tissue, comprising:

a housing defining an aperture over which the tissue can be placed;

a first thermal mass for inducing a transient temperature gradient in the tissue by means of conductive heat transfer with the tissue, the first thermal mass being infrared transmissive;

cooling means in operative combination with the first thermal mass for cooling the first thermal mass;

a second thermal mass for heating the tissue by means of conductive heat transfer with the tissue;

heating means in operative combination with the second thermal mass for heating the second thermal mass;

drive means mounted in the housing for alternately positioning the first and second thermal masses adjacent to the aperture to alternately heat and cool the living tissue;

infrared sensor means for detecting infrared emissions emanating from the tissue as the transient temperature gradient progresses into the tissue in use, and for providing output signals proportional to the detected infrared emissions; and data capture means for sampling the output signals provided by the infrared sensor means as the transient temperature gradient progresses into the tissue.

23. A spectrometer according to claim 22 wherein, in operation, the heating and cooling means are deactivated while the data capture means samples the output signals provided by the infrared sensor means as the transient temperature gradient progresses into the tissue.

24. A spectrometer for the non-invasive generation and capture of thermal gradient spectra from living tissue, comprising:

an enclosure including an infrared transmissive window over which the tissue can be placed;

a first thermal mass for inducing a transient temperature gradient in the tissue by means of conductive heat transfer with the tissue, the first thermal mass being infrared transmissive;

cooling means in operative combination with the first thermal mass for cooling the first thermal mass;

heating means in operative combination with the window for heating the window;

drive means mounted in the housing for alternately positioning the first thermal mass in a heat transfer relationship with the window;

infrared sensor means for detecting infrared emissions emanating from the tissue as the transient temperature gradient progresses into the tissue in use, and for providing output signals proportional to the detected infrared emissions; and data capture means for sampling the output signals provided by the infrared sensor means as the transient temperature gradient progresses into the tissue.

25. A spectrometer according to claim 24 wherein, in operation, the heating and cooling means are deactivated while the data capture means samples the output signals provided by the infrared sensor means as the transient temperature gradient progresses into the tissue.

26. A method for the non-invasive generation and capture of thermal gradient spectra from living tissue, comprising the steps of:

cooling a solid infrared transmissive thermal mass;

placing the solid infrared transmissive thermal mass into a conductive heat transfer relationship with the tissue thereby to generate a transient temperature gradient in the tissue;

detecting infrared emissions emanating from the tissue and passing through the solid infrared transmissive thermal mass;

providing output signals proportional to the detected infrared emissions; and sampling the output signals as the transient temperature gradient progresses into the tissue.

27. A method according to claim 26 wherein the step of placing the solid infrared transmissive thermal mass into a conductive heat transfer relationship further comprises the step of making direct contact between the tissue and the solid infrared transmissive thermal mass.

28. A method according to claim 26 wherein the conductive heat transfer relationship consists of contact between the solid infrared transmissive thermal mass and a relatively thin infrared transmissive window which is in direct contact with the tissue.

29. A method according to claim 26 further comprising the step of preheating the tissue before placing the solid infrared transmissive thermal mass into a conductive heat transfer relationship with the tissue.

* * * * *